United States Patent [19]

Mauze et al.

[11] Patent Number: 5,233,194
[45] Date of Patent: Aug. 3, 1993

[54] OPTICAL GAS SENSOR WITH ENRICHING POLYMER

[75] Inventors: Ganapati R. Mauze, Sunnyvale; Damien F. Gray, Mountain View, both of Calif.

[73] Assignee: Hewlett-Packard Company, Palo Alto, Calif.

[21] Appl. No.: 816,987

[22] Filed: Jan. 3, 1992

[51] Int. Cl.$^5$ .............................................. A61B 5/14
[52] U.S. Cl. .................................. 250/341; 128/634; 250/458.1; 356/41
[58] Field of Search .......................... 128/634; 356/41; 250/341, 459.1, 458.1

[56] References Cited

U.S. PATENT DOCUMENTS

| | | | |
|---|---|---|---|
| 4,201,222 | 5/1980 | Haase | 128/634 |
| 4,785,814 | 11/1988 | Kane | 128/634 |
| 4,800,886 | 1/1989 | Nestor | 128/634 |
| 5,142,155 | 8/1992 | Mauze et al. | 250/458.1 |

FOREIGN PATENT DOCUMENTS

| | | | |
|---|---|---|---|
| 0144713 | 10/1984 | European Pat. Off. | |
| 0259951 | 3/1988 | European Pat. Off. | 128/634 |

Primary Examiner—Constantine Hannaher

[57] ABSTRACT

A gas sensor using optical fiber technology to measure gas concentration in a test volume. In one embodiment, the sensor incorporates a gas enriching polymer which absorbs and concentrates carbon dioxide ($CO_2$) from the test volume surrounding the sensor. The polymer is wrapped around the core of an optical fiber which guides radiation with first selected wavelengths to the polymer. The radiation propagates into the polymer and reacts with the carbon dioxide in the polymer. Determination of $CO_2$ concentration in the test volume is made by measuring the amount of attenuation of the radiation after reacting with the carbon dioxide in the polymer. In another embodiment, the polymer is capable of absorbing oxygen from the test volume and oxygen concentration is measured using fluorescence quenching. Being added to the polymer, a special dye reacts to radiation having selected wavelengths and produces a second radiation with wavelengths which are different from the selected wavelengths and which are absorbed by oxygen. Determination of oxygen concentration in the test volume is made by measuring the degree of attenuation of the second radiation after reacting with the oxygen in the polymer.

24 Claims, 5 Drawing Sheets

OPTICAL GAS SENSOR WITH ENRICHING POLYMER

BACKGROUND OF THE INVENTION

This invention relates to sensors for detecting a gas in a test medium. More particularly, this invention relates to sensors that use electromagnetic absorption spectroscopy or fluorescence quenching spectroscopy for measuring the concentration of the gas in the test medium.

Using optical absorption measurements to find the concentration of a gas in a test medium is a method well known in the prior art. When radiation with a spectrum of wavelengths passes through a gas, a profile of absorption bands or the absorption spectrum of the gas can be obtained. Since each gas has its specific absorption spectrum, the type and quantity of the gas present in a sample can thus be specified via its absorption spectrum.

The medical profession has used gas sensors to monitor data such as gases in the blood of a surgical patient. Various medical personnel can track and evaluate the patient's metabolism and respiratory effectiveness from such data. There are prior art optical absorption gas sensors that are small enough to fit inside a catheter. This combination when inserted by an operator into a blood vessel permits continuous and instantaneous blood gas measurements.

The typical blood-gas sensors measure the optical absorption of the gas in the blood. The lowest gas concentration that can be detected in a test medium is the concentration that gives a detectable signal higher than the noise of the measuring system. Some carbon dioxide ($CO_2$) sensors operate at the strongly absorbed wavelengths around 4 $\mu$m (microns) for increased sensitivity. This entails the use of complex and expensive optical components to generate, filter, and measure these wavelengths. Making remote $CO_2$ measurements requires expensive optical fibers that have low absorption at these wavelengths in order to avoid interference with the measurement. Besides being excessively brittle for catheter use, these fibers have known reactivity with water that can compromise patient safety.

The medical profession has used commercially available gas sensors such as a Capnometer to measure the concentration of $CO_2$ in the airway stream of a patient. An operator mounts the $CO_2$ sensor on a breathing ventilator or breathing tube for monitoring the effectiveness of patient's ventilation. The sensor in the Hewlett Packard (HP) Capnometer (Model 47210) weighs several ounces, making it too heavy to be mounted on the airway tube of a neonate. The Novametrix Model 1260 Capnograph employs a sensor that weighs less than 1 ounce. However, in order to use this sensor with a neonate, that patient still must be intubated, as is the case for the HP instrument.

Other known airway devices operating at wavelengths around 4 $\mu$m typically use a heated light source to generate these wavelengths. This type of light source consumes a significant amount of electrical power and generates heat. This heat produces undesirable temperature gradients which adversely affect the measurement. Finally, many of these instruments are too inconveniently heavy to perch atop a breathing tube.

In a prior art thin film gas sensor, the refractive index of the measuring medium is very different from that of the sensing path capturing the optical radiation. The radiation used for detecting the concentration of the selected gas couples into the boundary layers of the measuring medium through total internal reflection. Since the radiation only reacts with the gas in the boundary layer of the measuring medium, a sufficiently long path is required to give a measurably accurate result. Moreover, this prior art device uses fluoride-glass fibers which, as mentioned previously, are expensive, excessively brittle and reactive when used in contact with moisture-bearing gas streams.

In summary, there is a need for a new gas sensor operating at wavelengths shorter than 4 $\mu$m in order to reduce the complexity and cost of sensor components. Furthermore, it is desirable for that new sensor to be more rugged, lightweight and compact than prior art gas sensors.

SUMMARY OF THE INVENTION

A new and improved sensor made according to the teachings of the present invention overcomes the problems and limitations of the previously mentioned prior art devices. The preferred embodiments of the invention monitor the concentration of a selected gas by measuring its degree of interaction with electromagnetic radiation having certain preferred wavelengths.

In a first embodiment of the present invention, a commercial grade optical fiber directs the selected radiation into a sensing path. The sensing path is a step index optical fiber with its buffer and cladding removed, exposing its core. A thin layer of measuring medium and another thin layer of reflecting membrane are coaxially mounted around the core. The sensing path with the measuring medium and the reflecting membrane form the sensor of the present invention. The reflecting membrane is permeable to the selected gas and the measuring medium has both a high diffusion coefficient and a high solubility for the selected gas. When the sensor is placed in a sample or test volume containing an unknown concentration of the selected gas, a portion of the selected gas passes into the sensor. A first electromagnetic radiation with at least one selected wavelength is transmitted into the measuring medium from the sensing path. The reflecting membrane bounces the radiation back into the measuring medium, preferably through total internal reflection. The selected gas, which has permeated into the measuring medium, partially absorbs the selected radiation. Measurement of the concentration of the selected gas in the sample volume is obtained by detecting the amount of radiation absorbed by the selected gas.

In a second embodiment of the present invention, the measuring medium includes an additional dye. The dye, when excited by the first electromagnetic radiation with at least one selected wavelength, correspondingly emits a second electromagnetic radiation of a different wavelength. This is known as the fluorescence of the dye. Not interacting with the first electromagnetic radiation, the selected gas quenches the fluorescence of the dye in accordance with the amount of the selected gas contained in the sensor. Thus, measurement of the concentration level of the selected gas is obtained by detecting the change in fluorescence due to the quenching caused by the selected gas.

In a third embodiment of the present invention, the measuring medium of the sensor is of the same type as that in the first embodiment. An optical fiber transmits the first electromagnetic radiation with one or more selected wavelengths into the measuring medium. The core at the end of the optical fiber is connected to one end of the measuring medium. A distal-end reflecting membrane is connected to the opposite end of the measuring medium. The first electromagnetic radiation after reacting with the selected gas in the measuring medium is returned by the distal-end reflecting membrane into the optical fiber. A conventional optical coupler then directs the radiation to an output path. Detection is then made of the amount of radiation absorbed by the selected gas so that a measurement is obtained of the concentration level of the selected gas.

In a fourth embodiment of the present invention, the sensor arrangement is similar to that in the third embodiment except the measuring medium includes a dye as in the second embodiment.

Additional embodiments of the present invention can be formed by mixing and matching the above four embodiments. For example, a further improved sensor made by combining the first and the second or the third and the fourth embodiments will detect two different selected gases. However, as will be explained, a few mutually exclusive conditions have to be met for that improved sensor to work. The first selected gas can only react with the first radiation but not the second or the dye-emitted radiation while the second selected gas can only react with the dye-emitted radiation but not the first or the second radiation. Further, the dye can only react with the second but not the first radiation.

A sensor made by combining the first and the third embodiments will have a relatively high volume of measuring medium. Since the concentration of the selected gas in the measuring medium will be greater than that in the sample volume, this sensor will detect a lower level of gas concentration than prior art sensors. Moreover, this increased sensitivity is achieved without requiring an increase or change in the sensitivity of any conventional radiation detectors which may be used with the present invention.

The first, second and third embodiments when combined also results in a sensor which has a relatively high volume of measuring medium and which can measure two selected gases. Again the mutually exclusive conditions of the selected gases only reacting with selected radiations must be met in order for this sensor to work.

The above-described and other features of the present invention will be more fully understood from a reading of the ensuing description given with reference to the appended drawings.

DESCRIPTION OF THE PREFERRED EMBODIMENTS

Figure 1:
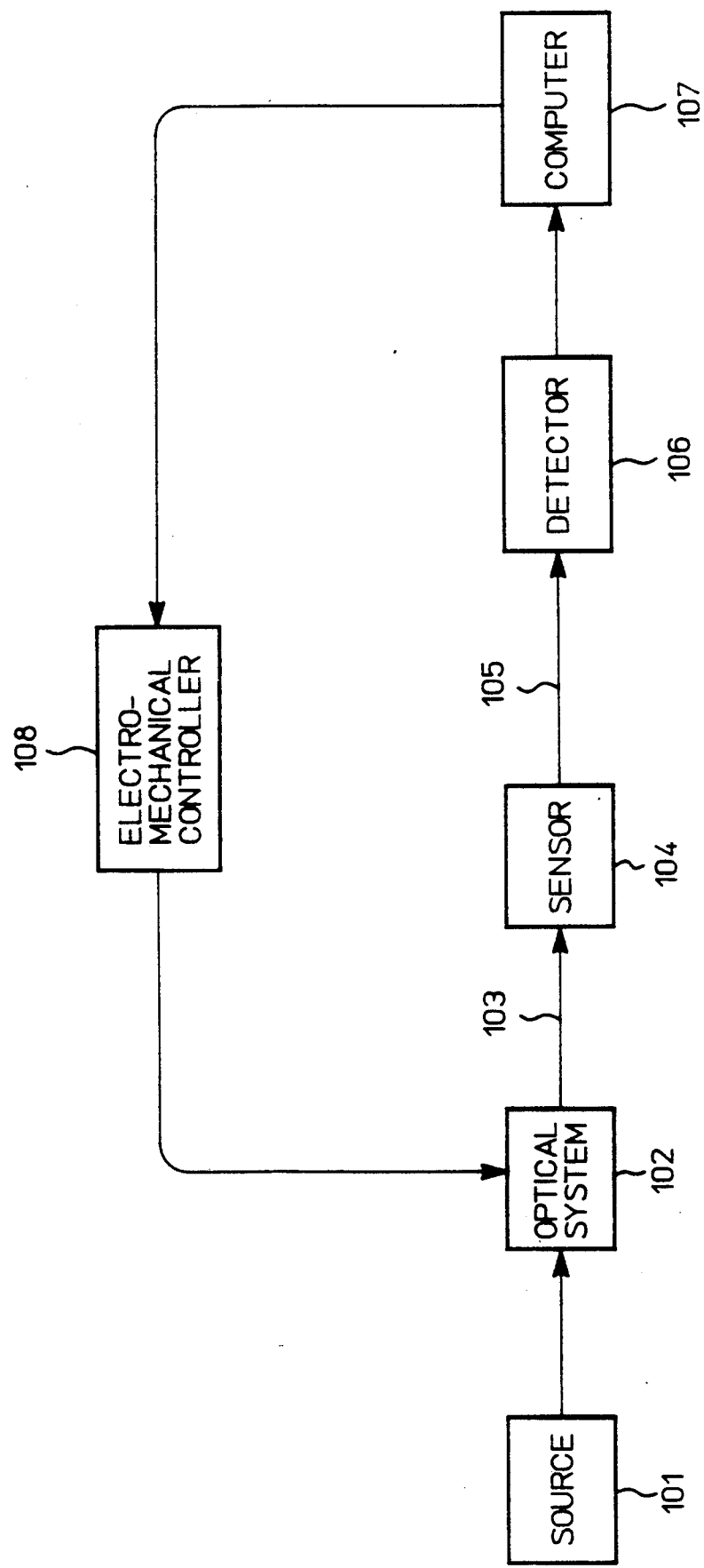
FIG. 1 is a block diagram showing a gas measuring system which incorporates either the first or second embodiments of the gas sensor made in accordance with the present invention.

FIG. 1 is a block diagram showing the first and second embodiments of the gas sensor made in accordance with the present invention and incorporated into a gas measurement system. An operator selects the gas of interest through a computer 107 which then picks a filter in an optical system 102 through an electromechanical controller 108. The filter in the optical system 102 passes one or more selected wavelengths of the optical radiation from the multiple wavelengths emitted by a source 101. The source 101 is preferably a halogen lamp GE787, made by General Electric. The optical system 102 focuses the selected optical radiation into an input optical fiber 103 that is a commercial grade gradient index or step index optical fiber. In the first embodiment of the present invention arranged for detecting $CO_2$, the selected wavelengths are from a group which includes wavelengths of about 1.6 $\mu$m and from a range between 1.9 and 2.05 $\mu$m. In the second embodiment of the present invention arranged for detecting $O_2$ (oxygen), the wavelength of the selected radiation is about 450 nm (nanometer). The input fiber 103 guides the radiation to a sensor 104 that is in a test medium which contains an unknown level of the gas of interest, namely $CO_2$ or $O_2$. An output optical fiber 105 being the same material as the input optical fibers 103, connects to the output of the sensor. For the selected radiation, the optical fiber 103 and 105 have greater than 90% spectral transmission. Moreover, the fiber is impermeable to the selected gas (and is malleable). The output fiber 105 directs the radiation which passes through the sensor 104 to a detector 106. In the present invention, the detector is preferably an ETX 300-GR22, manufactured by Epitaxx at Princeton N.J. The detector 106 measures the intensity of the passed-through radiation and the computer 107 which receives the output from the detector 106 operates to produce a measurement of the level of selected gas in the test medium.

Figure 2:
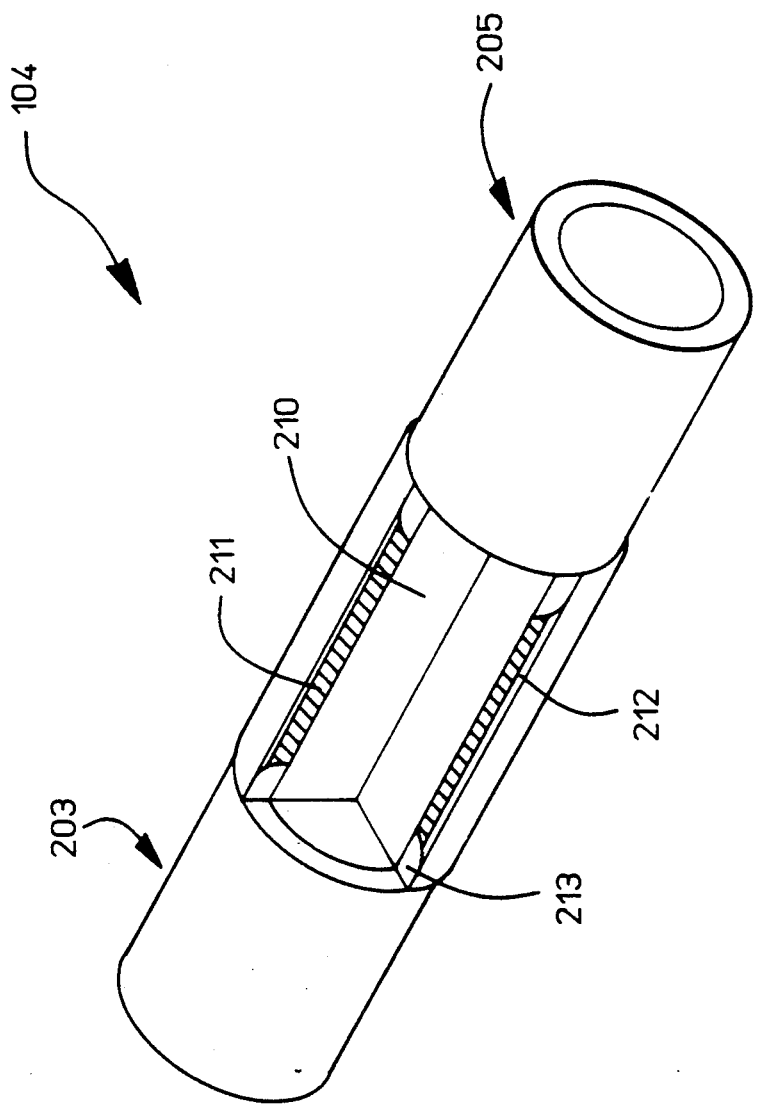
FIG. 2 is a sectional view of the first and second embodiments of the present invention.

FIG. 2 depicts a sectional view of the sensor 104 shown in FIG. 1. The sensor 104 is made from a step index optical fiber, such as a PCS Anhydroguide Vis IR Fiber by Fiberguide Industries, with the buffer and cladding removed exposing the core of the fiber. One preferred material for the fiber core 210 is fused silica with a refractive index of 1.46. The sensor 104 has a gas-enriching polymer 211 coaxially mounted to the fiber core 210.

Due to geometrical considerations, for a given thickness of gas enriching polymer, the larger the core of the fiber, the less sensitive the sensor will be. The thickness of the gas enriching polymer 211 is determined by the response time needed. The diameter of the fiber core 210 is determined by such considerations as the signal variation needed, the source brightness, and the ease of fabrication of the sensor 104. In first and second working embodiments of the present invention, a fiber with a core diameter of 800 $\mu$m was used to make fabrication relatively simple. However, an optimal diameter is believed to be in the range between 50 and 100 $\mu$m.

The gas-enriching polymer 211 selected for the first and second embodiments of the present invention has a high diffusion coefficient for gases such as $O_2$ and $CO_2$. The diffusion coefficient of a gas in a polymer measures the diffusion speed of the gas. High diffusion coefficient implies quick equilibrium between the gas in the polymer and the test medium. The quicker a sensor equilibrates with the gas in the test medium, the quicker the sensor can respond to changes in the concentration of the gases in the test medium. In other words, a high diffusion coefficient sensor means a sensor with a fast response time. This is essential for some patient monitoring applications.

The selected gas enriching polymer also has high solubility for gases such as $O_2$ and $CO_2$. The solubility of a gas in a polymer is the concentration of gas in the polymer compared to the concentration of gas in air having the same volume as the polymer and under standard temperature and pressure. High solubility is synonymous to high enrichment factor that is one main element of a high sensitivity sensor.

The refractive index of the gas-enriching polymer 211 is preferably very close to the refractive index of the core of the step index optical fiber in the optical radiation with the selected wavelengths. This results in significant amounts of the radiation in the step index optical fiber being propagated into the gas-enriching polymer and reacting with the gas in the polymer.

In the first embodiment of the present invention for measuring $CO_2$, the reduction in intensity of the optical radiation absorbed by the $CO_2$ is a measure of the concentration of $CO_2$ in the test medium. Carbon dioxide strongly absorbs the radiation with a wavelength of 4.26 $\mu$m and weakly absorbs the radiation having wavelengths from 1.9 to 2.05 $\mu$m and 1.6 $\mu$m in the measuring medium. In the present invention which preferably uses radiation having wavelengths that are weakly absorbed, compensation for the reduction in absorption is via the enrichment factor of the polymer 211. Since the $CO_2$ concentration in the polymer 211 is higher than in the test medium, the reduction in absorption is compensated by the increase in concentration. Working in the wavelengths around 1.9 to 2.05 $\mu$m and 1.6 $\mu$m is desirable because that arrangement allows the use of inexpensive and rugged communication grade step index optical fibers. Thus, there is no need to use the expensive, reactive and brittle fluoride fibers for radiation with longer wavelengths. The length of a working first embodiment of the sensor is 8 cm and the optimal length of the sensor is believed to be about 50 cm.

The second embodiment of the present invention measures $O_2$. The detection of $O_2$ is based on the phenomenon of fluorescence quenching using a dye dissolved in the polymer. A preferred dye is tris(4,7-diphenyl-1,10 phenanthroline) ruthenium II dichloride. When a first radiation having a wavelength of 450 nm excites a molecule of the dye, a second radiation with a wavelength of 670 nm will be emitted. If the excited molecule of the dye collides with an $O_2$ molecule, the module of the dye will be quenched and will not emit the second radiation. The probability of collision is proportional to the concentration of $O_2$ in the polymer. Therefore, by measuring the intensity of the second radiation at 670 nm, the concentration of $O_2$ in the polymer is determined.

Tables 1 and 2 show some examples and properties of materials suitable for the measuring medium 211, with the enriching factor being designated as ENR FAC. One preferred measuring medium 211 is a polymer known as poly(trimethylsilylpropyne). The solubility of $CO_2$ in this material is about 11.6 cubic centimeter (cc) per cc of the polymer at 25° C. and one atmospheric pressure. This means that the concentration of $CO_2$ is 11.6 times higher in the polymer than in the same volume of air at same temperature and pressure. At 35° C., the solubility of $CO_2$ is about 7.7 and $O_2$ in this polymer is about 5.14. The solubility of $O_2$ is not as essential because $O_2$ significantly quenches the radiation emitted by the dye.

TABLE 1

| POLYMER | ENR FAC at 35° C. |
|---|---|
| Poly(trimethylsilyl-propyne) | 7.7 |
| 2,6-dimethyl-1,4 poly(phenylene oxide) | 6.6 |
| Polyimide from 3,3',4,4'-bisphenyltetracarboxylic di-anhydride (BPDA) and 4,4'-diaminodiphenylsulfone | 15.3 |
| Polyimide from phenylmaleiimide dianhydride (PMDA) and 4,4'-oxydianiline (ODA) | 11.6 |
| Polyimide from BPDA and ODA | 8.9 |
| Polyimide from 1,2,4-tricarboxy-3-carboxymethylcyclopentane dianhydride and 4 4'-oxydianiline (ODA) | 16.0 |
| Poly(phenolphthalein phthalate) | 11.3 |
| Tetrabromo-polycarbonate | 7.8 |
| Tetrachloro-polycarbonate | 7.2 |
| Tetramethyl-polycarbonate | 7.1 |
| Polysulfone | 6.1 |
| Polyetherimide | 6.0 |
| Polyarylate | 5.5 |
| Polycarbonate | 4.6 |
| Polystyrene | 1.8 |

TABLE 2

| Properties of Poly(trimethylsilyl-propyne) | | | |
|---|---|---|---|
| GAS | TEMP °C. | ENR FAC | DIFFUSION COEFFICIENT |
| $CO_2$ | 35 | 7.7 | $2.63 * 10^{-5}$ |
| $O_2$ | 35 | 5.14 | $3.96 * 10^{-5}$ |

On the other hand, $CO_2$ does not absorb as well for radiation around 1.9 to 2.05 $\mu$m and 1.6 $\mu$m so a higher concentration of $CO_2$ for reaction with the radiation is needed. The diffusion coefficient of $O_2$ and $CO_2$ in the polymer 211 is in the order of $10^{-5}$ cm$^2$/second which is about three to five orders of magnitude higher than most other polymers. The refractive index of the polymer is about 1.46. It is almost the same as the fiber core. The length of a working second embodiment of the sensor is 8 cm and the optimal length of the sensor is about 50 cm.

With reference to FIG. 2, in both the first and the second embodiments of the present invention, a reflecting membrane 212 coats the gas enriching polymer 211. The refractive index of the reflecting membrane 212 is lower than the refractive index of the polymer and the fiber core. This reflecting membrane 212 is very permeable to the selected gas but the membrane bounces the optical radiation preferably through total internal reflection back into the polymer 211. One example of the reflecting membrane 212 is DuPont "TEFLON AF" with a refractive index of 1.23. The compound "TEFLON AF" is made of 1,3-dioxole, 4,5-difluoro-2,2-bis (trifluoromehtyl)-,polymer with tetrafluoroethene. Another type of reflecting membrane is porous gold. The trade-off regarding the thickness of the reflecting membrane 212 is the amount of reflection to the permeability of the gas. An extremely thin layer of gold or a highly porous gold will be very permeable to the gas but does not give sufficient reflection to the radiation.

If the test medium does not affect the surface property of the measuring medium 211 of the sensor when the reflecting membrane 212 is removed, that reflecting membrane may not be needed. In other words, because air or vacuum has a refractive index of 1.00 that is significantly less than that of the gas-enriching polymer 211, any of the radiation in the sensor is captured within the polymer and the core of the fiber. If the test medium affects the surface property of the measuring medium 211, the reflecting membrane 212 supplies a controlled environment for the sensor 104.

The gas-enriching polymer 211 and the reflecting membrane 212 are very thin to minimize the diffusion time of the selected gas and the response time of the sensor 104. In addition, the sensor is relatively more malleable if the layers are thin. On the other hand, the polymer 211 has to have enough volume to give sufficient detectable signal and the reflecting membrane 212 has to be thick enough to trap the radiation in the polymer. To give sufficient volume for the polymer 211, one can either have a thick polymer or a long sensing path. Since a thick polymer 211 would decrease the response time of the sensor, the preferred arrangement is a sensing path with sufficient length. The length required depends on the signal to noise ratio of the gas measurement system. The detected signal should be preferably more than twice the noise level of the gas measuring system. Typical thickness for the polymer 211, poly(-trimethylsilylpropyne), is from 10 to 50 $\mu$m and the preferred thickness is 10 $\mu$m. Typical thickness for the "TEFLON AF" reflecting membrane 212 is about 5 microns.

Figure 3:
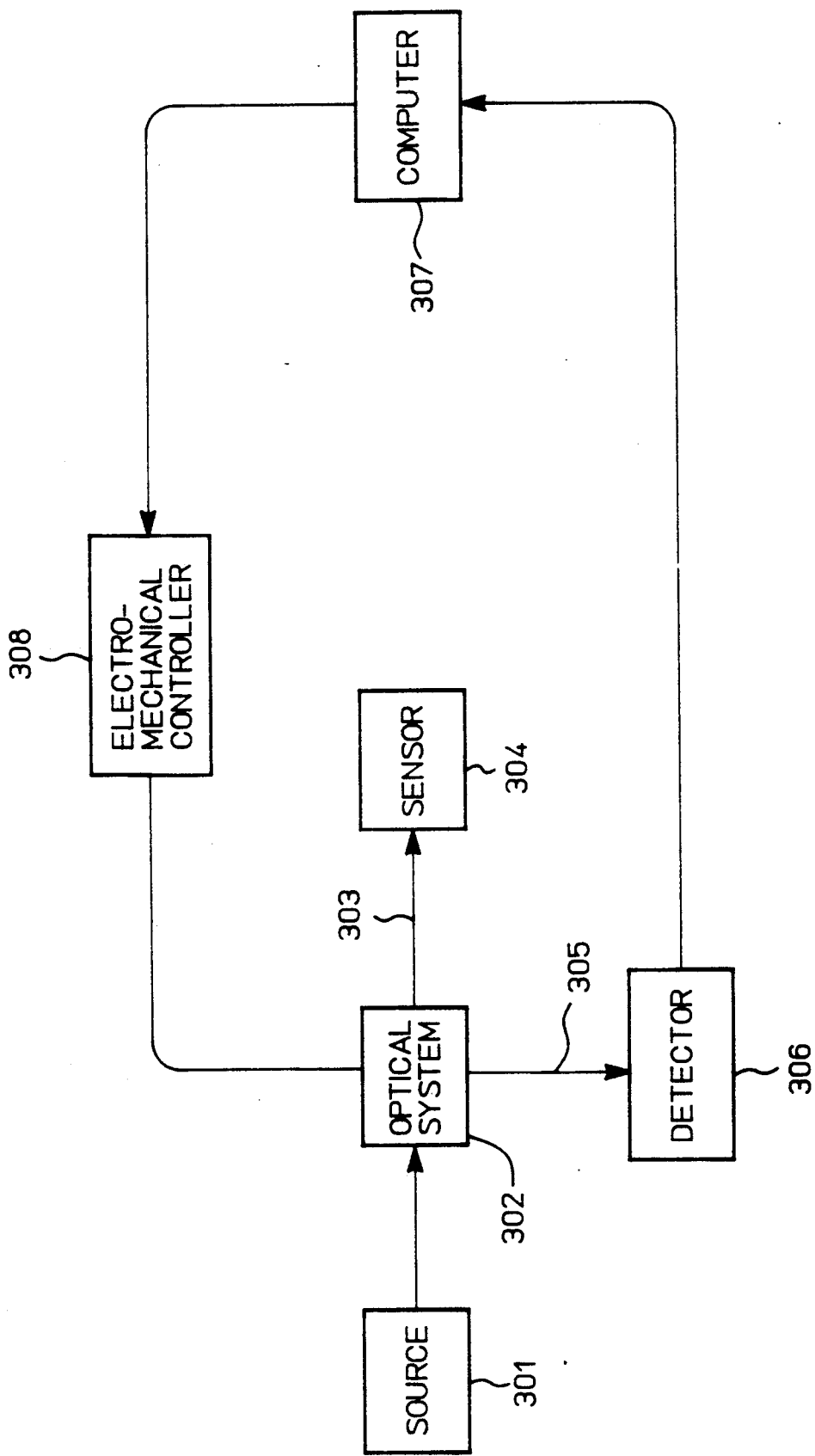
FIG. 3 is a block diagram showing a gas measuring system which incorporates either the third or fourth embodiments of the gas sensor made in accordance with the present invention.

FIG. 3 is a block diagram showing the gas measuring system which incorporates either the third or fourth embodiments of the gas sensor made in accordance with the present invention. An operator selects the gas of interest through a computer 307 which then picks a filter in an optical system 302 through an electromechanical controller 308. The filter passes one or more wavelengths of the optical radiation from the multiple wavelengths emitted by a source 301. The optical system 302 focuses the radiation through an input fiber 303 to a sensor 304. The sensor 304, as will be described below, reflects the radiation passing through the sensor back to the optical fiber 303 and towards the optical system 302. The optical system 302 couples the reflected radiation to an output fiber 305 that transmits such radiation to a detector 306. The detector 306 measures the intensity of the reflected radiation and the computer 307 which receives the output from the detector 306 operates to produce a measurement of the level of selected gas in the test medium.

Figure 4:
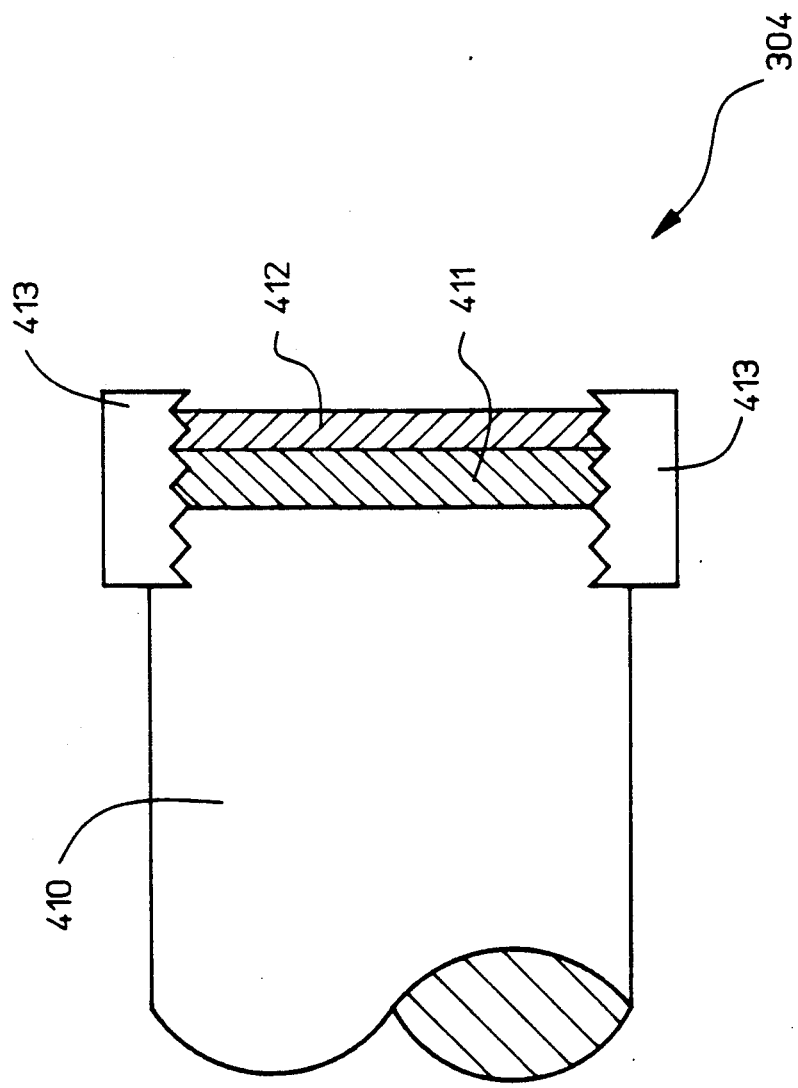
FIG. 4 is a sectional view of the sensor depicted in FIG. 3.

FIG. 4 depicts a sectional view of the sensor 304. The third embodiment of the sensor in the present invention measures the concentration of $CO_2$ with the same measuring medium as in the first embodiment. The fourth embodiment of the present invention measures the concentration of $O_2$ with the same measuring medium as in the second embodiment. The third embodiment thus does not include a dye which is included in the measuring medium of the fourth embodiment. As depicted in FIG. 4, the sensor 304 as used in the third and fourth embodiments has a measuring medium 411 and a distal-end reflecting membrane 412 at the end of an optical fiber 410. The fiber 410 is cut at the distal-end to expose its core. The fiber can be either a gradient index optical fiber or a step index optical fiber. The measuring medium 411 with a distal-end reflecting membrane 412 are then coaxially abutted to the core. A reflecting membrane 413 fastens the fiber 410 and the polymer 411 with the distal-end reflecting membrane 412 together. The reflecting membrane 413 is preferably made of the same material as the reflecting membrane in the first and second embodiments of the present invention or can be made of silicone rubber. The measuring medium 411 is preferably made of the same material as the measuring medium of the first and the second embodiments of the present invention. The distal-end reflecting membrane 412 is designed to be highly reflective, which would be the case if it was made of metal, in order to return any of the radiation which may be incident perpendicularly onto the distal-end reflecting membrane.

It should be noted that additional embodiments of the present invention are formed by mixing and matching the above four embodiments. A sensor through combining the first and second or the third and fourth embodiments will detect two different selected gases, such as $O_2$ and $CO_2$. Since both gases are in the same gas enriching polymer, the dye selected is chosen so that it does not react with the radiation used to detect $CO_2$. Similarly, $CO_2$ should not quench the fluorescence of the dye, nor should it react with the radiation used to detect $O_2$. Furthermore, $O_2$ should not react with the wavelengths of any radiation that cause the fluorescence of the dye nor react with the wavelengths of any radiation used to detect $CO_2$.

The sensor fabricated through combining the first and the third embodiments will have a relatively high volume of measuring medium. With this high volume of enriching polymer, the sensor will capture more gas leading to a more sensitive sensor than prior art sensors. The gas enriching polymer is coaxially mounted around the core and at the end of the optical fiber.

The first, second and third embodiments when combined also results in a sensor with a relatively high volume of enriching polymer for measuring two selected gases. Again the previously-described, mutually-exclusive conditions of the selected gases and the dye only reacting with selected wavelengths of the radiation must be met in order for proper operation of this form of the present invention.

Figure 5:
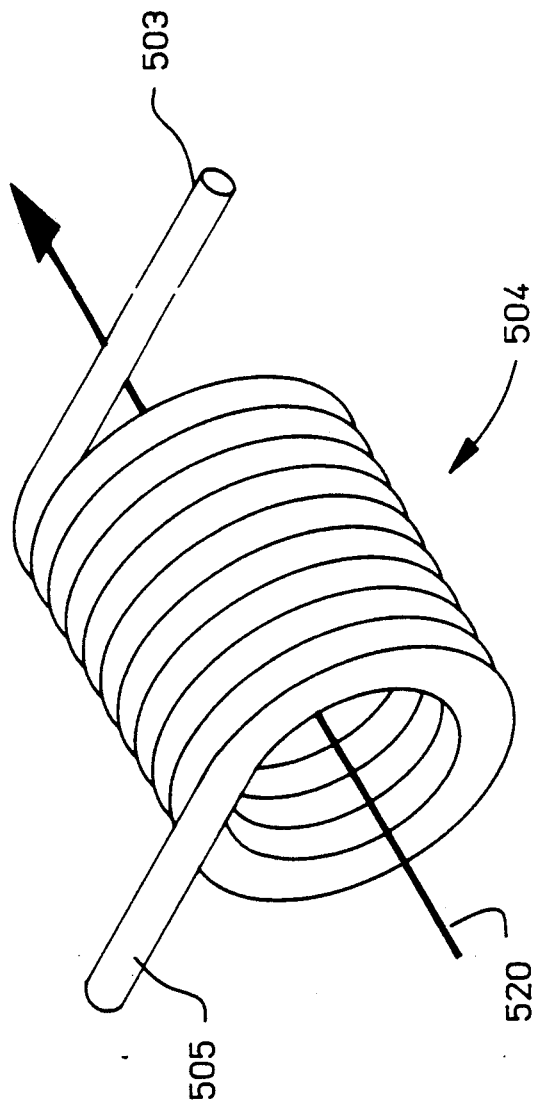
FIG. 5 is another embodiment of the present invention.

FIG. 5 shows another configuration of the present invention made with a long sensing path. It is desirable to have a high volume of measuring medium because increasing the volume increases the sensitivity of the sensor. One way to achieve high volume is by making the measuring medium thicker. However, a thick polymer adversely affects the response time of the sensor because more time is needed for the selected gas to diffuse into the gas-enriching polymer. A preferred method to increase the volume without increasing the response time is by making the sensing path longer. FIG. 5 shows a preferred embodiment having a long sensing path within a small area by coiling the sensing path. This configuration is feasible because the present invention is malleable.

The process to make the sensors

I. One approach to make the first embodiment of the present invention is as follows:
  1. Scribe the step index optical fiber to cut the fiber.
  2. Remove the buffer and the cladding of the sensing portion of the fiber for the sensing path (such as slightly longer than 8 cm) by the following steps:
     a. Dip the sensing portion into room temperature concentrated acetic acid for 30 minutes or till the buffer is loose.
     b. Use a blade to cut along the circumference of the fiber to remove the buffer.
     c. Dip the fiber into DI water to clean the fiber.
     d. Dip the sensing portion into concentrated nitric acid (about 2 molar) for 30 minutes or until the cladding is loose or dissolves.
     e. Use a brush to remove the cladding.
     f. Dip the fiber into DI water to clean the fiber.

3. Clean the enriching medium in toluene solution from the manufacturer by the following steps:
   a. Mix the solution in large quantity of hot methanol (about 50° C.).
   b. Use standard filtration technique to filter out the enriching medium after the enriching medium precipitates.
   c. Dry the enriching medium.
   d. Dissolve the enriching medium (about 5% weight) into toluene.
   e. Repeat the steps from a to d until the toluene solution becomes transparent. This might take about 3 times repetitions.
4. Coat the sensing portion with the enriching medium by the following steps:
   a. Dip the sensing portion into the toluene solution with 5% weight of the filtrated enriching medium at room temperature.
   b. Remove the sensing portion from the toluene solution and let the solvent evaporate in an enclosed container with toluene vapor so that the solvent evaporates slowly. This evaporation process takes about 2 hours.
   c. Check for discontinuities in the coating under a magnification of 30 times.
   d. Repeat the steps from a to c if there are discontinuities in the coating.
5. Coat the sensing portion with a reflecting medium to make the sensor by the following steps:
   a. Prepare a 0.5% weight solution of "TEFLON AF" in Fluorinert fluorocarbon solvent (FC 72, boiling point 56° C.) at room temperature.
   b. Dip the sensing portion with the enriching medium the TEFLON AF solution.
   c. Remove the sensing portion and let the solvent evaporate in air for about 8 hours.
   d. Check for discontinuities in the coating under a magnification of 30 times.
   e. Redo step b to d if there are discontinuities in the coating.
6. Optically polish the tip of the sensor and the tip of another piece of optical fiber and bind the two tips with an optical grade adhesive such as Norland NOA 61. Cure the adhesive.

II. One proposed approach to make the second embodiment of the present invention is as follows:
1. Repeat steps 1 to 3 of section I.
2. Dissolve 5 grams of the enriching medium and 0.001 to 0.02 grams of the dye into 100 grams of Chloroform at room temperature.
3. Repeat steps 4 to 6 of I except replacing the toluene solution with chloroform solution.

III. One approach to make the third embodiment of the present invention is as follows:
1. Scribe the optical fiber to cut the fiber.
2. Clean the enriching medium as in step 3 of I till the toluene solution is transparent.
3. Place the toluene solution with the enriching medium into a TEFLON container where the cavity shape is the shape of the polymer desired. Slowly evaporate off the toluene to leave behind the enriching medium.
4. Evaporate a thin film of gold (a few microns) onto all surfaces of the enriching medium.
5. Optically polish one surface of the gold plated enriching medium and optically polish the surface of the optical fiber with the exposed core.
6. Bind the two polished surfaces with an optical grade adhesive such as Norland NOA 61. Cure the adhesive.

IV. One proposed approach to make the fourth embodiment of the present invention is as follows:
1. Repeat step 1 and 2 as in III.
2. Filter out the enriching medium and dissolve 5 grams of the enriching medium and 0.001 to 0.02 grams of the dye into 100 grams of Chloroform at room temperature.
3. Place the chloroform solution with the enriching medium and the dye into a TEFLON container where the cavity shape is the shape of the polymer desired. Evaporate off the chloroform to leave behind the enriching medium.
4. Repeat step 4 to 6 as in III.

While the present invention has been described with reference to several embodiments, it will be apparent that improvements and modifications may be made within the purview of the invention without departing from the true spirit and scope thereof as defined in the appended claims. For example, the present invention can be made to be small enough for mounting near the end of a fiber optic cable and for insertion into the throat of a patient, including a neonate, without intubation. In addition, even though the preferred embodiments of the present invention use optical radiation for the detection of only $CO_2$ and $O_2$, other wavelengths of radiation may be used for those applications where it is desirable to detect other fluids by measuring absorption spectra in other regions, such as but not limited to the ultraviolet, infrared or microwave wavelengths.

We claim:
1. A gas measurement sensor using electromagnetic radiation for detecting a selected gas in a test medium, said sensor comprising:
   a transmission path for receiving a first electromagnetic radiation with at least one selected wavelength; and
   a measuring medium circumferentially coupling to said transmission path so that said first electromagnetic radiation is propagated circumferentially into said measuring medium, said measuring medium including a material for enhancing the concentration of said selected gas in said measuring medium relative to the concentration of said gas in said test medium when said sensor is immersed in said test medium.

2. A sensor as recited in claim 1 further comprising:
   a reflecting membrane being substantially permeable to said selected gas and being connected for reflecting said first electromagnetic radiation back into said measuring medium.

3. A sensor as recited in claim 2, wherein said selected gas reacts with said first electromagnetic radiation.

4. A sensor as recited in claim 3, wherein:
   said transmission path comprises a core portion of a step index optical fiber;
   said measuring medium is characterized by a refractive index; and
   said reflecting membrane is characterized by a refractive index less than said refractive index of said measuring medium.

5. A sensor as recited in claim 4, wherein:
   said selected gas is carbon dioxide;
   said first electromagnetic radiation includes one selected wavelength chosen from a group comprising approximately 1.6 microns and approximately between 1.9 to 2.05 microns; and said material is poly(trimethylsilyl-propyne).

6. A sensor as recited in claim 5, wherein said reflecting membrane is 1,3-dioxole, 4,5-difluoro-2,2-bis(trifluoromehtyl)polymer with tetrafluoroethene.

7. A sensor as recited in claim 6, wherein said transmission path has a diameter approximately between 50 to 800 μm.

8. A sensor as recited in claim 2 further comprising:

a dye dissolved in said measuring medium, upon excitation by said first electromagnetic radiation, for emitting a second electromagnetic radiation having at least one selected wavelength, each selected wavelength of said second electromagnetic radiation being different from each selected wavelength of said first electromagnetic radiation, said reflecting membrane being connected for reflecting said second electromagnetic radiation back into said measuring medium; and wherein said selected gas quenches said second electromagnetic radiation.

9. A sensor as recited in claim 8, wherein:

said transmission path comprises a core portion of a step index optical fiber;

said measuring medium is characterized by a first refractive index; and said reflecting membrane is characterized by a second refractive index that is less than said first refractive index of said measuring medium.

10. A sensor as recited in claim 9, wherein:

said selected gas is oxygen;

said first electromagnetic radiation has one wavelength about 450 nanometers;

said material is poly(trimethylsilyl-propyne); and said dye is tris(4,7-diphenyl-1,10 phenanthroline) ruthenium II dichloride.

11. A sensor as recited in claim 10, wherein said reflecting membrane is 1,3-dioxole, 4,5-difluoro-2,2-bis(-trifluoromehtyl)polymer with tetrafluoroethene.

12. A sensor as recited in claim 8 further comprising:

a different selected gas;

a third electromagnetic radiation with at least one selected wavelength radiating into said measuring medium; and wherein said measuring medium enhances the concentration of said different selected gas in said measuring medium relative to the concentration of said different selected gas in said test medium when said sensor is immersed in said test medium, said reflecting membrane is substantially permeable to said different selected gas and being connected for reflecting said third electromagnetic radiation back into said measuring medium, said different selected gas only reacts with said third electromagnetic radiation, said dye and said selected gas are unreactive with said third electromagnetic radiation.

13. A gas measurement sensor using optical radiation for detecting a selected gas in a test medium, the sensor comprising:

a measuring medium receiving a first optical radiation with at least one selected wavelength shorter than 4 μm, said first optical radiation propagating into said measuring medium, said measuring medium including a material for enhancing the concentration of said selected gas in said measuring medium relative to the concentration of said selected gas in said test medium when said sensor is immersed in said test medium, said measuring medium having a first end and an opposing second end;

a distal-end reflecting membrane being connected to said second end of said measuring medium for reflecting said first optical radiation back through said measuring medium.

14. A sensor as recited in claim 13, further comprising:

a fastening reflecting membrane being substantially permeable to said selected gas and connected for fastening said measuring medium to said distal-end reflecting membrane and for reflecting said first optical radiation back into said measuring medium.

15. A sensor as recited in claim 14, wherein said selected gas reacts with said first optical radiation.

16. A sensor as recited in claim 15, wherein said distal-end reflecting membrane is a metal.

17. A sensor as recited in claim 16, wherein:

said selected gas is carbon dioxide;

said first optical radiation includes one selected wavelength chosen from a group comprising approximately 1.6 microns and approximately between 1.9 to 2.05 microns; and said material is poly(trimethylsilyl-propyne).

18. A sensor as recited in claim 17, wherein said fastening reflecting membrane is 1,3-dioxole, 4,5-difluoro-2,2-bis (trifluoromehtyl)-,polymer with tetrafluoroethene.

19. A sensor as recited in claim 13 further comprising:

a dye dissolved in said measuring medium, upon excitation by said first optical radiation, emitting a second optical radiation having at least one selected wavelength, each selected wavelength of said second optical radiation being different from each selected wavelength of said first optical radiation, said distal-end reflecting membrane being connected for reflecting said second optical radiation back through said measuring medium;

a fastening reflecting membrane being substantially permeable to said selected gas and connected for fastening said measuring medium to said distal-end reflecting membrane and for reflecting said first optical radiation back into said measuring medium; and wherein said selected gas quenches said second optical radiation.

20. A sensor as recited in claim 19, wherein:

said measuring medium is characterized by a first refractive index; and said fastening reflecting membrane is characterized by a second refractive index which is less than said first refractive index of said measuring medium.

21. A sensor as recited in claim 20, wherein:

said selected gas is oxygen;

said first optical radiation has one wavelength about 450 nanometers;

said material is poly(trimethylsilyl-propyne); and said dye is tris(4,7-diphenyl-1,10 phenanthroline) ruthenium II dichloride.

22. A sensor as recited in claim 21, wherein said fastening reflecting membrane is 1,3-dioxole, 4,5-difluoro-2,2-bis (trifluoromehtyl)-,polymer with tetrafluoroethene.

23. A method to make a gas measuring sensor with a reflecting membrane and a first medium on a step index optical fiber which has a buffer and a cladding and a core, said method comprising the steps of:

a. stripping said buffer and said cladding to expose said core of said fiber;
b. coating said exposed core of said fiber with said first medium to make a medium-coated fiber;
c. preparing a solution of 1,3-dioxole, 4,5-difluoro-2,2-bis (trifluoromehtyl)-, polymer with tetrafluoroethene; and
d. coating said medium-coated fiber with 1,3-dioxole, 4,5-difluoro-2,2-bis (trifluoromehtyl)-,polymer with tetrafluoroethene by said solution of 1,3-dioxide, 4,5-difluoro-2,2-bis (trifluoromehtyl)-,polymer with tetrafluoroethene.

24. A gas measurement sensor using electromagnetic radiation for detecting a selected gas in a test medium, said sensor comprising:

a transmission path for receiving a first electromagnetic radiation with at least one selected wavelength, said transmission path being characterized by a first refractive index;

a measuring medium coupled to said transmission path, said first electromagnetic radiation propagating into said measuring medium, said measuring medium including a material for enhancing the concentration of said selected gas in said measuring medium relative to the concentration of said selected gas in said test medium when said sensor is immersed in said test medium; and a reflecting membrane being substantially permeable to said selected gas and being connected for reflecting said first electromagnetic radiation back into said measuring medium, said reflecting membrane being characterized by a second refractive index which is less than said first refractive index.

* * * * *